(12) United States Patent
Carroll et al.

(10) Patent No.: US 11,519,539 B2
(45) Date of Patent: Dec. 6, 2022

(54) DEVICES, SYSTEMS, AND METHODS FOR A REDUCER WITH AN INTEGRATED SEAL

(71) Applicant: Repligen Corporation, Waltham, MA (US)

(72) Inventors: Derek Carroll, Los Angeles, CA (US); Bao Le, Waltham, MA (US)

(73) Assignee: Repligen Corporation, Waltham, MA (US)

( * ) Notice: Subject to any disclaimer, the term of this patent is extended or adjusted under 35 U.S.C. 154(b) by 542 days.

(21) Appl. No.: 16/666,970

(22) Filed: Oct. 29, 2019

(65) Prior Publication Data

US 2020/0132231 A1 Apr. 30, 2020

Related U.S. Application Data

(60) Provisional application No. 62/751,947, filed on Oct. 29, 2018.

(51) Int. Cl.
*F16L 25/14* (2006.01)
*F16L 21/03* (2006.01)

(52) U.S. Cl.
CPC .............. *F16L 25/14* (2013.01); *F16L 21/03* (2013.01)

(58) Field of Classification Search
CPC ......... F16L 21/03; F16L 21/022; F16L 23/16; F16L 23/18; F16L 23/22; F16L 23/04; F16L 23/12; F16L 25/14; F16L 13/00; F16L 13/16; F16L 13/12
USPC .......... 285/335, 336, 337, 364, 295.1, 295.3
See application file for complete search history.

(56) References Cited

U.S. PATENT DOCUMENTS 2,867,463 A * 1/1959 Snider .................. F16L 25/023
277/614
2009/0179388 A1 7/2009 Uhlenkamp et al.
2010/0078395 A1 4/2010 Shevitz
2010/0320699 A1 12/2010 Takeda et al.
2011/0140374 A1 6/2011 Dubiel
(Continued)

FOREIGN PATENT DOCUMENTS

CN 206973113 U 2/2018
DE 1945986 A1 4/1970
(Continued)

OTHER PUBLICATIONS

International Search Report and Written Opinion dated Jan. 16, 2020 for PCT application No. PCT/US2019/58489 filed Oct. 29, 2019.
(Continued)

*Primary Examiner* — Aaron M Dunwoody
(74) *Attorney, Agent, or Firm* — KDB Firm PLLC (57) ABSTRACT

The present disclosure is related to bioprocessing devices, systems, and methods, and particularly to sanitary connections for bioprocessing. The devices, systems, and methods described herein can relate to the sanitary connection of flow fittings, such as reducers, with considerations for ease of assembly and sealing. In some embodiments, the system may include a flow reducer, a ferrule and a gasket. The flow reducer may include a gasket channel, an overmold channel within the gasket channel, and one or more cavities within the overmold channel. The gasket may be overmolded within the gasket channel and extending within the one or more cavities.

12 Claims, 7 Drawing Sheets

(56) References Cited

U.S. PATENT DOCUMENTS

2012/0074694 A1* 3/2012 Butte ................. F16L 23/12
                                                      277/609
2017/0321831 A1 11/2017 Nahrwold et al.

FOREIGN PATENT DOCUMENTS

| EP | 1130304 A2 | 9/2001 |
| EP | 2426280 A1 | 3/2012 |
| JP | S50122765 A | 9/1975 |
| JP | 2008240916 A | 10/2008 |
| JP | 6411688 B1 | 10/2018 |
| WO | 2007126892 A2 | 11/2007 |

OTHER PUBLICATIONS

European Search Report and Written Opinion for Application No. EP19880844, dated Jul. 8, 2022, 11 pages.

* cited by examiner

DEVICES, SYSTEMS, AND METHODS FOR A REDUCER WITH AN INTEGRATED SEAL

PRIORITY

This application claims the benefit of priority under 35 USC § 119 to U.S. Provisional Patent Application Ser. No. 62/751,947, filed Oct. 29, 2018, which is incorporated by reference herein in its entirety and for all purposes.

FIELD

The present disclosure is related to bioprocessing devices, systems, and methods, and particularly to sanitary connections for bioprocessing. The devices, systems, and methods described herein can relate to the sanitary connection of flow fittings, such as reducers, with considerations for ease of assembly and sealing.

BACKGROUND

Bioprocessing encompasses the research, development, manufacturing, and commercialization of products prepared from or used by biological systems, including food, feed, fuels, biopharmaceuticals, cosmetics, and the like. Biologically derived materials such as bacteria, enzymes, chloroplasts or the like may be altered and/or applied for use in beneficial products. Cell manufacturing processes may be separated into upstream processes and downstream processes. The upstream process may include the entire process from early cell isolation and cultivation to cell banking and culture expansion of the cells until final harvest, termination of the culture, and collection of the live cell batch. The upstream process may refer to the first step in which microbe cells are grown. For example, bacterial or mammalian cell cultures in bioreactors. Upstream processing may involve all the steps related with inoculum development, media development, improvement of inoculum by genetic engineering processes, and optimization of growth kinetics for improving product development. After product development, the product may be purified for a desired quality. When a desired quality and density is achieved, the batch may be harvested and fed into the downstream process. The downstream process may include the portion of bioprocessing where the cell mass from the upstream process is further processed to meet a desired quality and purity. Downstream processing may be divided into cell disruption, purification, and polishing. Distillation may separate out desirable mass from remainder mass to be discarded.

Filtration is typically performed to separate, clarify, modify and/or concentrate a fluid solution, mixture, or suspension. In the biotechnology, pharmaceutical, and medical industries, filtration is vital for the successful production, processing and analysis of drugs, diagnostics, chemicals as well as many other products. As examples, filtration may be used to sterilize fluids or gases, clarify a complex suspension into a filtered "clear" fraction and an unfiltered fraction; similarly, constituents in a suspension may be concentrated by removing or "filtering out" the suspending medium. Further, with appropriate selection of filter material, filter pore size or other filter variables, many other specialized filter uses have been developed; these may involve selective isolation of constituents from various sources, including, cultures of microorganisms, blood, as well as other fluids that may be solutions mixtures or suspensions. With further advancements in cell and recombinant DNA technologies many new products are being developed, many of which are so complex that they can only be produced by the complex synthetic machinery of live cells, using cell culture techniques. Filtration may be used to enhance the productivity of such cell cultures; by maintaining the cultures for extended periods at high cell concentrations at high productivity and by providing a product stream more amenable to further processing and purification.

With advancements in new materials, manufacturing methods and requirements in recent years, the construction and use of disposable equipment has gained increasing acceptance. The use of disposable bags as cell culture bioreactors and storage vessels has become more common. Such disposable containers can be "set-up" with minimal handling and do not require cleaning or sterilization by the user. They are supplied clean, sterile and in a form ready for use, at great savings in cost and reduced handling by the user; furthermore, at the end of their use, the bags can be readily discarded without disassembly or cleaning. However, there is still user handling involved in setting up these systems, which may result in user errors that compromise the systems.

Tri-Clover (TC) style fittings are frequently used in bioprocessing and other applications that may be sensitive to bacterial growth due to their hygienic union of different processing elements. These are typically composed of 2 identical ferrules of the fittings to be joined, a sanitary gasket to form a seal between the two ferrules, and clamp to provide the necessary force to maintain the seal under pressure. The process to make this union and create the necessary flow path involves simultaneously needing to align the 2 ferrules of the element that are being joined with a seal in between them while at the same time securing a clamp. This process can be cumbersome in some situations that can create difficulty for users and may lead to leaks or non-hygienic unions in misassembled connection. A common fitting that utilizes these connections are reducers which can join 2 different sizes of TC connection (e.g. 6" TC to 2" TC). Such ferrules and/or fittings with varying diameters may connect parts into systems that have dissimilar inflow or outflow diameter flow lumens.

Flow connections among current bioprocessing systems include multiple cumbersome parts for the user to handle in creating a sanitary tight seal for a flow path. These systems may be susceptible to user error that may compromise the sterility and/or seal of a flow connection.

SUMMARY

This disclosure is intended to simplify bioprocessing flow connections by incorporating a sanitary gasket into a fitting to result in a single component. Reducing the number of components for a user to handle may simplify the union process in creating a sanitary and leak-proof flow path.

In various embodiments of a bioprocessing flow connection system, a system may include a flow reducer. The flow reducer may include a first end with a first aperture and a first diameter. A second end may include a second aperture and a second diameter that may be different than the first diameter. A reducer lumen may extend through the first and the second ends. A reducer rim may be about the first end and about the first aperture. A gasket channel may be in the reducer rim and may extend about the first aperture. A ferrule may be substantially aligned with the flow reducer. The ferrule may have a ferrule lumen through a ferrule aperture. A ferrule rim may be about the ferrule aperture. An alignment channel may be about the ferrule rim. A gasket may be disposed within the gasket channel comprising. An alignment rib may be disposed on an outer surface of the gasket. The alignment rib may extend about the first aperture. The alignment rib may be configured to substantially align with the alignment channel of the ferrule. The gasket may be an overmold within the gasket channel. An overmold channel may be within the gasket channel. The overmold channel may extend about the first aperture and toward the second end. One or more cavities within the overmold channel may extend radially away from the reducer lumen. The gasket may extend within the one or more cavities. A plurality of concentric friction channels may be within the reducer rim extending about the lumen. The gasket may extend within the friction channels. A primary rib may be disposed on the outer surface of the gasket concentrically within the alignment rib. An inner surface of the gasket may taper inwardly toward both of the reducer rim and the reducer lumen. The inner surface may increase surface contact with the reducer rim as pressure increases within the lumen. The reducer rim may include a reducer rib about the first aperture that may be in substantial contact with an outer surface of the inner surface of the gasket. A secondary rib may be disposed on the outer surface of the gasket concentrically between the alignment rib and the primary rib. A stop may be disposed on the outer surface of the gasket and may extend about an outer edge of the gasket. The stop may have a surface tapering radially toward the reducer lumen. A process vessel may be substantially aligned with the second end of the flow reducer. The ferrule may be part of a filtration vessel.

In another aspect, a gasket may include an outer surface. An inner surface may oppose the outer surface. An aperture may extend through the outer and inner surfaces. An alignment rib may be disposed on the outer surface. The alignment rib may extend about the aperture. The alignment rib may be configured to substantially align with an alignment channel of a ferrule rim. A primary rib may be disposed on the outer surface of the gasket concentrically within the alignment rib. An inner edge of the gasket may taper inwardly toward the aperture. The gasket may be configured for overmolding within a ferrule. The gasket may include silicone. A material of the ferrule may include a different material than the gasket. A stop may be disposed on the outer surface of the gasket and may extend about an outer edge of the gasket. The stop may have a surface tapering radially toward the aperture. A secondary rib disposed on the outer surface of the gasket concentrically between the alignment rib and the primary rib.

In another aspect, a filtration system may include a flow reducer including a first rim about a lumen. A gasket channel may be in the first rim and may extend about the lumen. A gasket may be overmolded within the first rim. A flow reducer may be substantially aligned with the gasket. A clamp may be about the flow reducer and ferrule. The clamp may compress the flow reducer and ferrule toward each other. An alignment rib may be disposed on an outer surface of the gasket and may extend about an aperture of the gasket. The alignment rib may be configured to substantially align with an alignment channel of the ferrule. An overmold channel may be within the first rim. One or more cavities may be within the overmold channel extending radially outward. The gasket may extend within the one or more cavities. A primary rib may be disposed on an outer surface of the gasket. An inner edge of the gasket may taper inwardly toward an inner edge of the first rim. A secondary rib may be disposed on the outer surface of the gasket concentrically outside of the primary rib. The reducer may be disposed between a fluid feed and a tangential flow for hollow fiber filtration unit.

DETAILED DESCRIPTION

Overview

Bioprocessing requires flow connections that are sanitary and leak-proof. A flow connection (e.g., a tri-clover connection) including two ferrules having an open-faced rim is desirable for such connections because their connection points are easily visible by the user and are easily cleaned. There is little hidden surface area in such connection ferrules for particulates to cling to that the user is unable to see and access for cleaning. A properly installed gasket between the ferrules creates a sanitary tight fit that includes a seal to prevent leaks. A user may assemble a flow connection by first placing a first component having a ferrule (such as a filter, reducer, or the like) on a level surface with a flow path facing upwards so that gravity may assist in guiding the remaining parts into place. The user may then remove a gasket from its packaging and may coat the gasket in a liquid compatible with the flow path components (e.g., deionized water, or the like) to increase flexibility of the gasket. The user may then position the gasket into the ferrule and gently guide the gasket and its features to fit into the channel(s) of the ferrule. The user may then evenly press downwardly about the circumference of the gasket without distorting its shape to attempt a good fit of the gasket with the ferrule. The user may then place a compatible component having a second ferrule (e.g., a reducer fitting, pressure transducer, or the like) on top of the gasket, attempting to ensure that the features of the gasket align and fit with the second ferrule. The user may then balance the assembly together and wrap a clamp around the two ferrules and gasket before tightening the clamp. A clamp that has two or more tightening mechanisms should be tightened at the same time or in a patterned alternation to ensure even pressure about the connection. Installing the clamp completes the connection assembly. However, a user may mishandle the gasket by bringing it into contact with body oils, debris or the like, causing it to no longer be sanitary. The user may also improperly install the gasket through misalignment, asymmetrical alignment, over tightening, under tightening, or asymmetrical tightening, such that the seal is compromised, causing leaks. The gasket may also not properly fit within a ferrule due to manufacturing tolerances that may prevent a fit to function as a seal.

Figure 1:
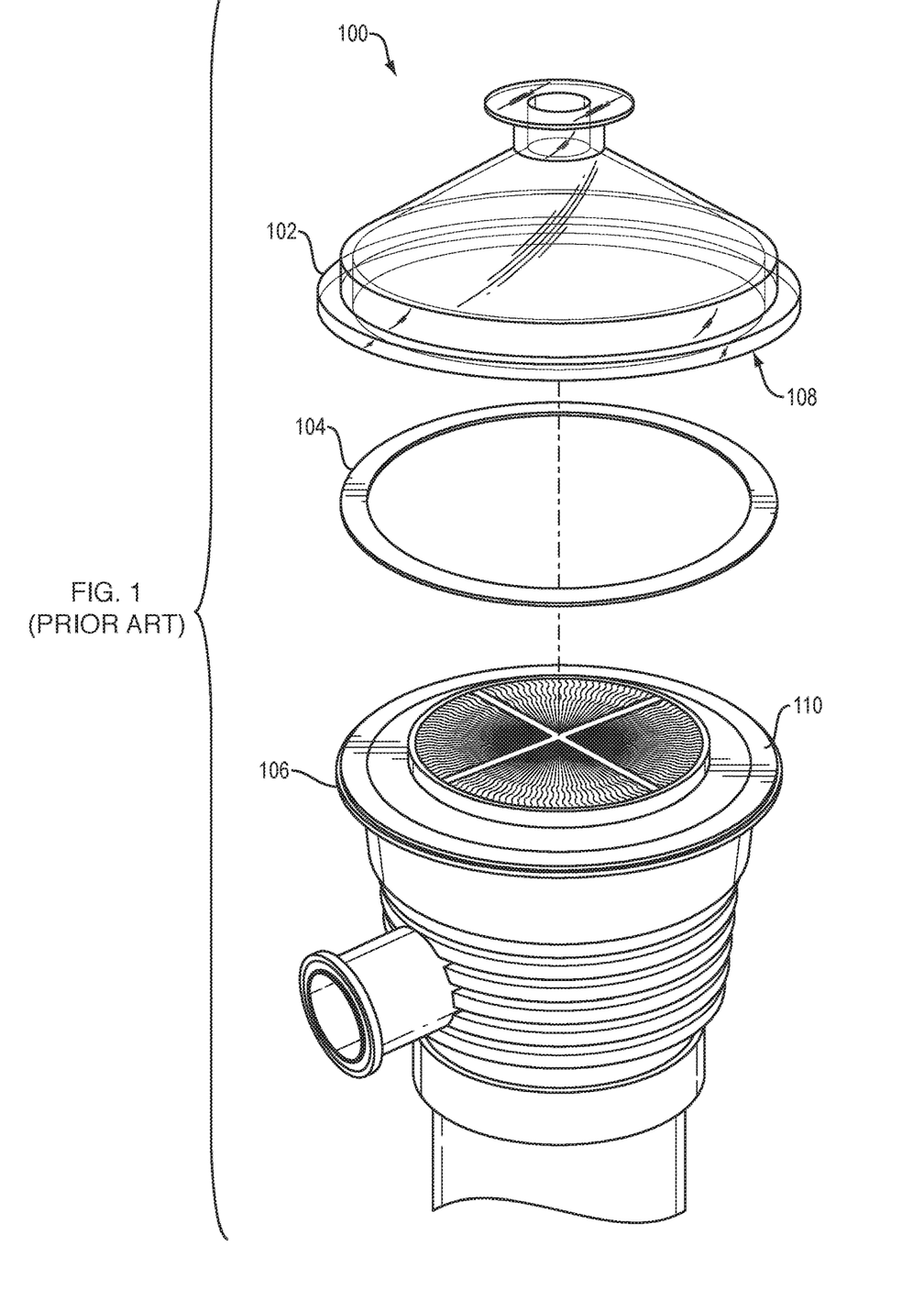
FIG. 1 illustrates an exploded view of a flow connection, in accordance with an embodiment of the present disclosure.

Referring to FIG. 1, a prior art exploded flow connection assembly 100 is illustrated. A first ferrule 102 of a flow reducer is positioned over a gasket 104. The gasket 104 aligns with and fits into the rim 108 of the first ferrule 102. The gasket 104 also aligns with and fits into the rim 110 of the second ferrule 106, which is a filter.

A flow connection assembly may include a clamp installed about a sequence of two ferrules with a gasket therebetween. The clamp may be wrapped about the ferrules and gasket and tightened by, e.g., one or more screws and/or a hinge, such that the clamp is brought into further contact with the ferrules and/or the gasket. The clamp may force the ferrules closer together, which bring some surfaces of the ferrules into contact or into closer contact with the gasket. This forcing of the ferrules closer together may compress the gasket, causing a better fit of the gasket into the ferrules and/or a stronger gasket seal against forces created by the flow of fluids through the flow connection.

Figure 2:
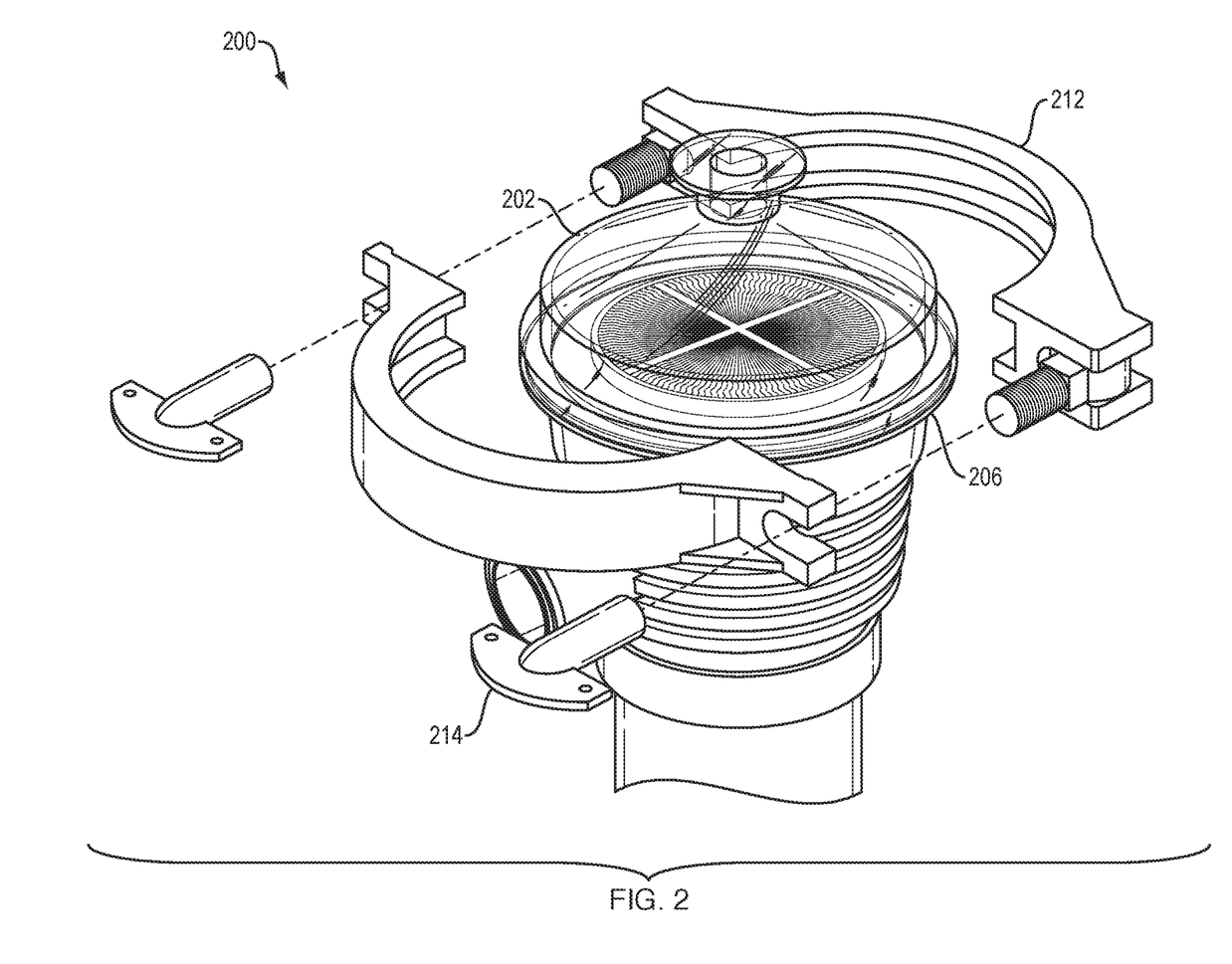
FIG. 2 illustrates an exploded view of a clamp about a flow connection, in accordance with an embodiment of the present disclosure.

Referring to FIG. 2, an embodiment of a bioprocessing flow connection system 200 is illustrated including an exploded clamp 212. The exploded clamp 212 is disassembled about a first ferrule 202, a second ferrule 206, and a gasket therebetween (not shown). The clamp 212 includes two tightening nuts 214 for a user to manipulate by hand for completing assembly of the flow connection system 200 and for further tightening and/or loosening the clamp 212.

Figure 3A:
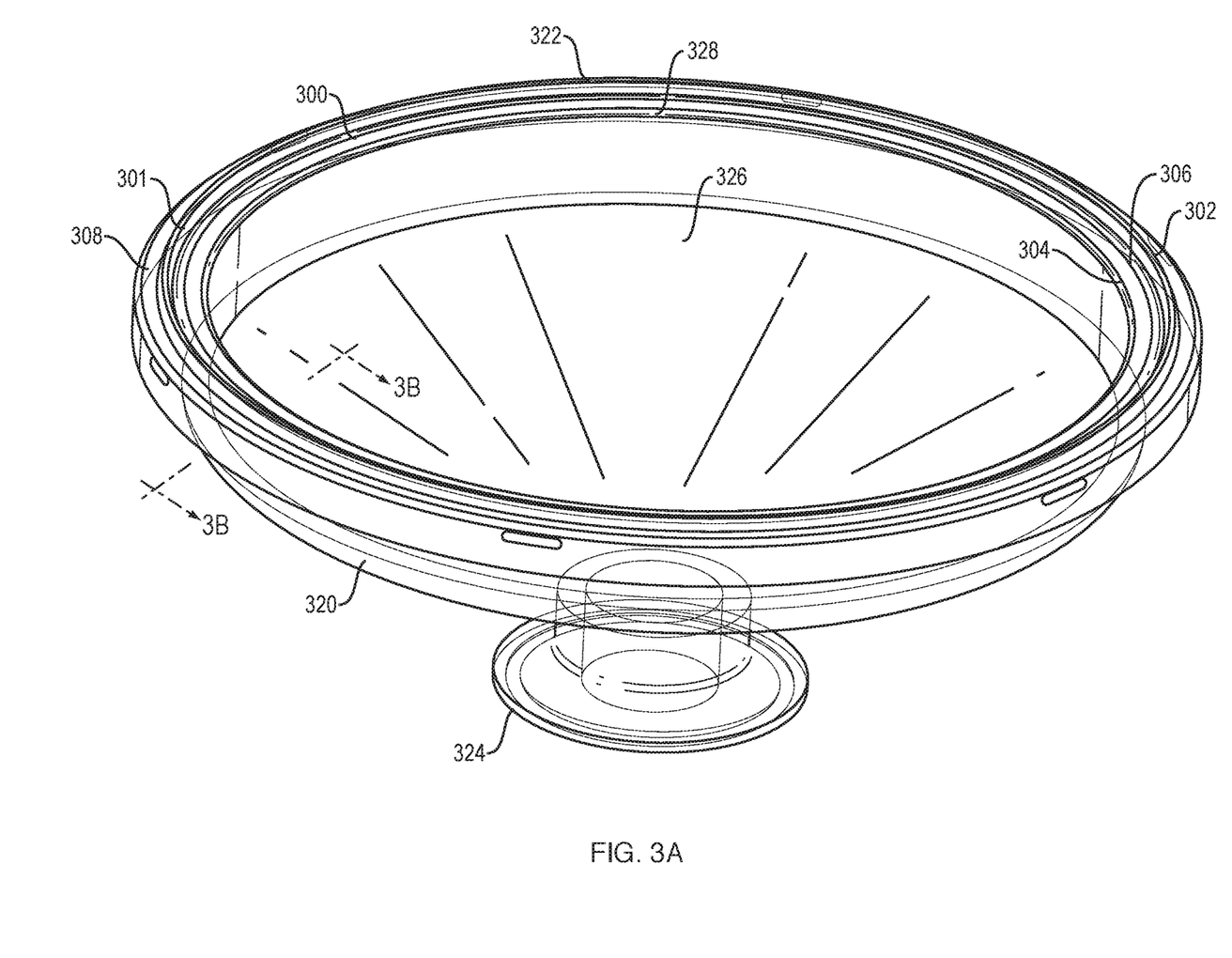
FIGS. 3A-3C illustrate a gasket within a reducer, in accordance with an embodiment of the present disclosure.
Figure 3B:
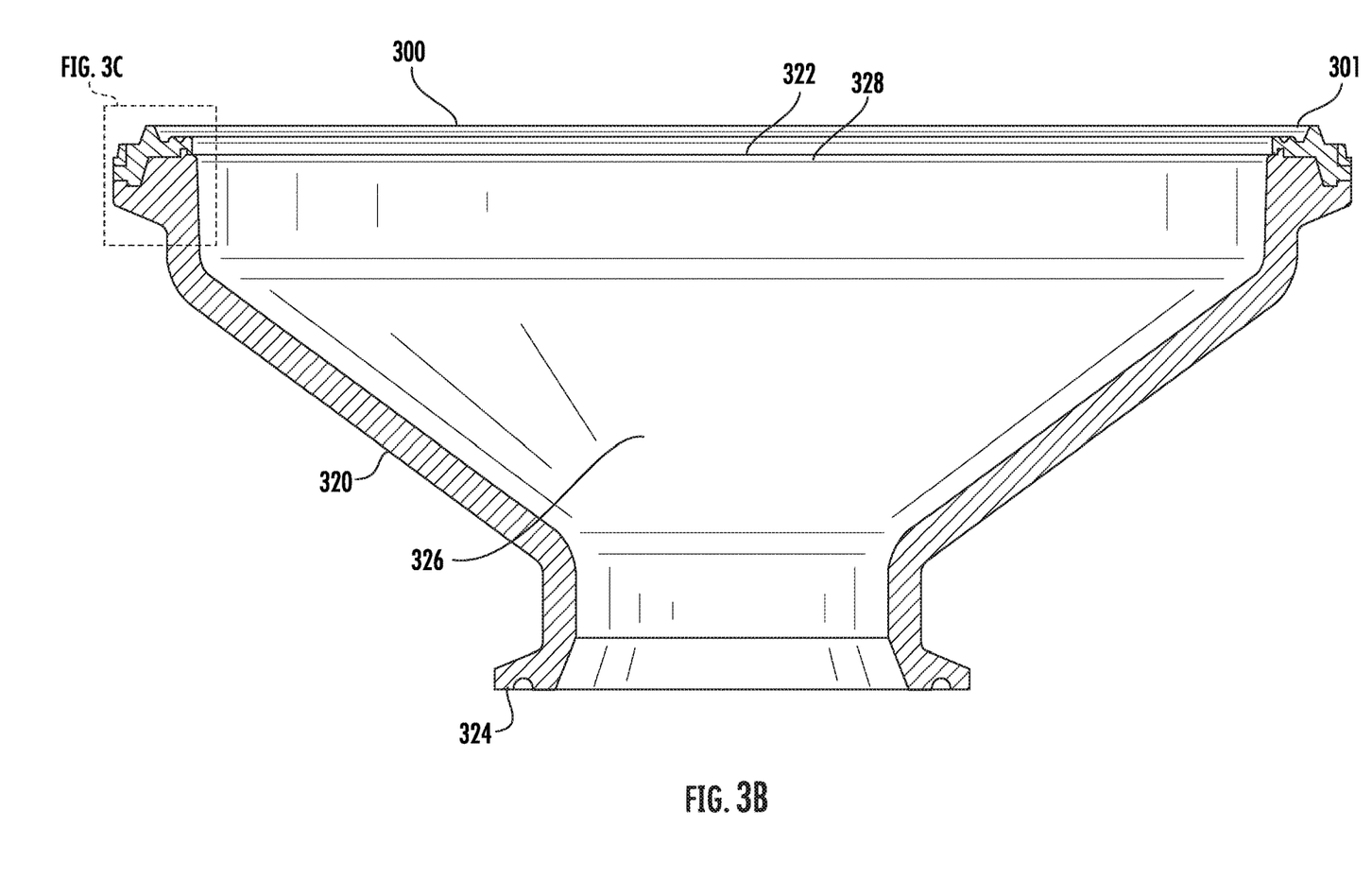
Figure 3C:
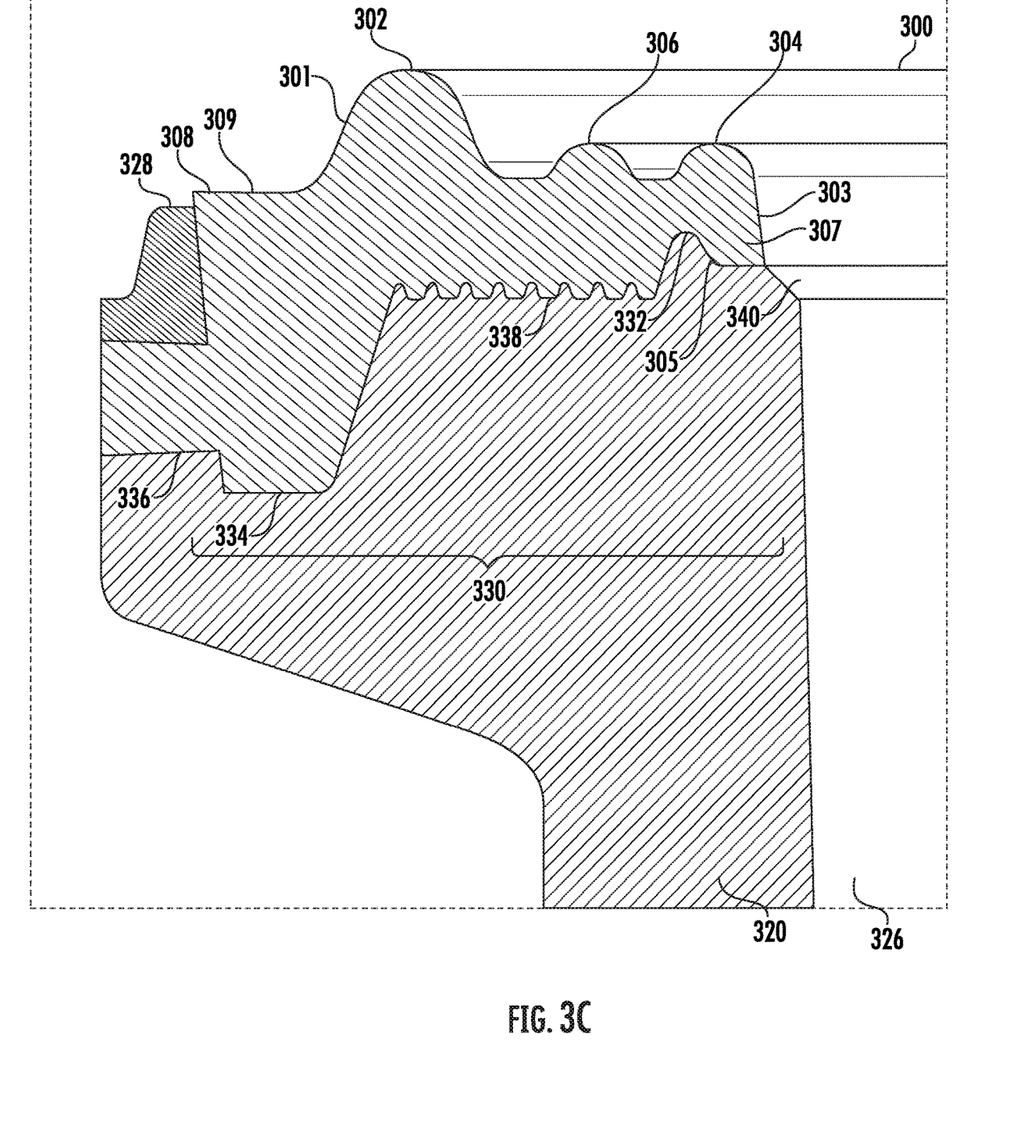

Referring to FIGS. 3A-3C, an embodiment of a bioprocessing flow connection system is illustrated including a flow reducer 320 having a first end 322 with a first aperture with a diameter that is larger than the diameter of a second end 324. A reducer lumen 326 extends through the first end 322 and the second end 324. The reducer lumen 326 is a variable diameter lumen that is a flow path for a fluid through a flow connection. A reducer rim 328 extends about the first end 322 and about the first aperture. The reducer rim 328 has a gasket channel 330 extending about the rim 328. A gasket 300 is disposed within the gasket channel 330. The gasket 300 has an alignment rib 302 disposed on an outer surface 301 of the gasket 300 that extends about the gasket 300 and about the first aperture. The alignment rib 302 is configured to substantially align with an alignment channel of another rim of a ferrule. A primary rib 304 is disposed on the outer surface of the gasket 300 concentrically within the alignment rib 302. An inner edge of the gasket 300 is the terminus of a taper 307 that tapers inwardly from the primary rib 304 toward both of the reducer rim 328 and the reducer lumen 326. The reducer rim 328 also includes a reducer rib 332 about the first aperture in substantial contact with an outer surface 305 of the taper 307. A secondary rib 306 is disposed on the outer surface 301 of the gasket 300 and is concentrically between the alignment rib 302 and the primary rib 304. A positive stop 308 is disposed on the outer surface 301 of the gasket 300 and extends about the outer edge of the gasket 300. The positive stop 308 has a surface 309 tapering radially toward the reducer lumen 326 and tapering axially toward the second end 324. The outer surface 303 of the taper 307 may be substantially continuous with an inner surface 340 of the ferrule rim. The gasket 300 is overmolded into the gasket channel 330 of the reducer 320. The gasket channel 330 includes portions for the gasket 300 to be overmolded into. These portions include an overmold channel 334 in the gasket channel 330 that extends about the first aperture and also extends (i.e., has a depth that extends) toward the second end 324. The overmold channel 334 has numerous cavities 336 that extend radially away from the reducer lumen 326 that the gasket 300 extends into. There are six cavities 336 extending radially about the reducer 320. The cavities 336 extend through the reducer 320 at these points, creating cavity apertures. The gasket channel 330 also includes eight concentric friction channels 338 within the gasket channel 330 that extend about the reducer lumen 326. The gasket 300 is overmolded into these friction channels 338.

Figure 4A:
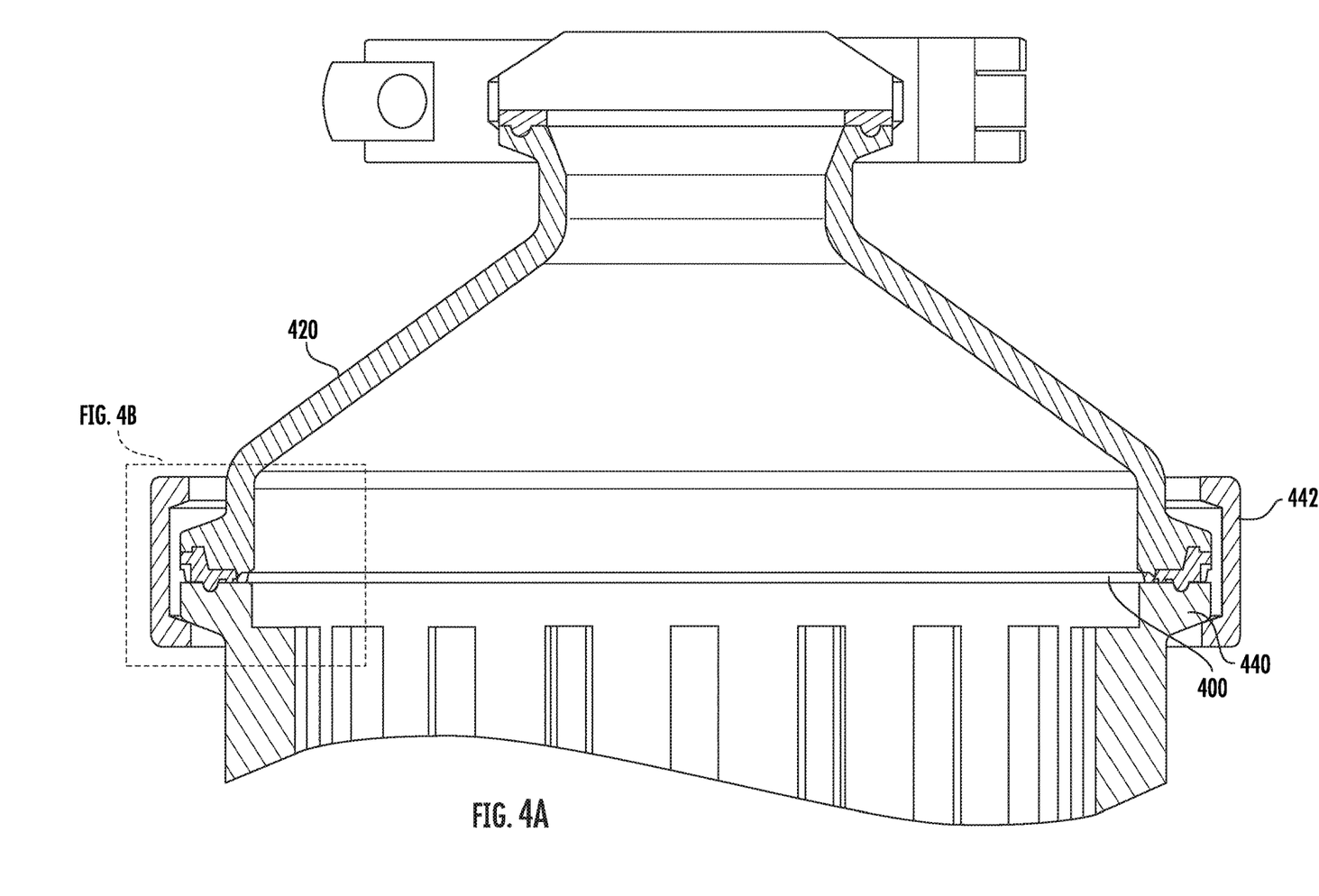
FIGS. 4A and 4B illustrate an assembled flow connection, in accordance with an embodiment of the present disclosure.
Figure 4B:
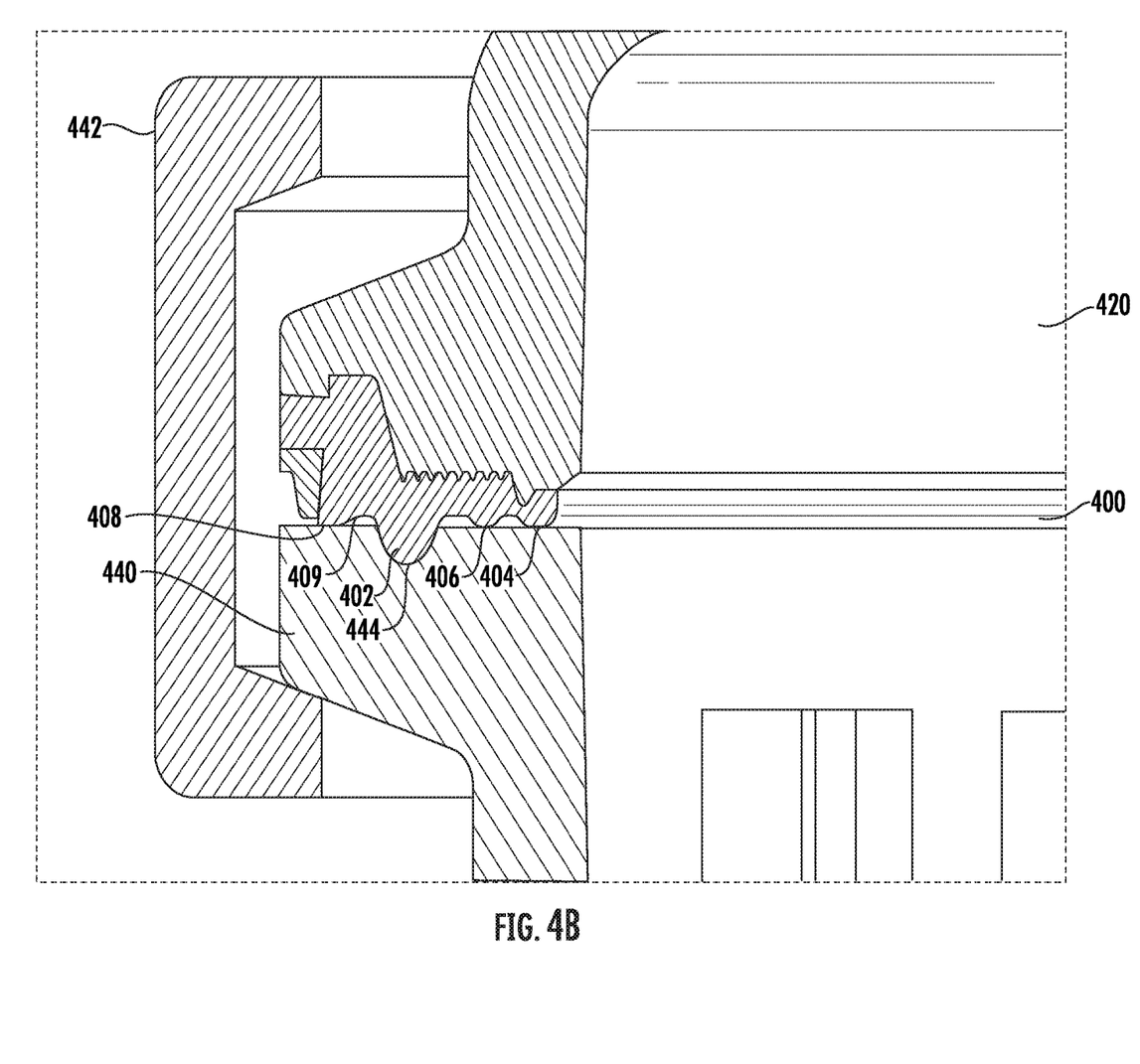

Referring to FIGS. 4A and 4B, an embodiment of a bioprocessing flow connection system is illustrated including a flow reducer 420 having an overmolded gasket 400. A ferrule 440 opposes the flow reducer 420 and is in substantial contact with the gasket 400. The reducer 420, ferrule 440, and gasket 400 are all forced together by the clamp 442. The reducer 420, gasket 400, and ferrule 440 create a flow lumen therein for a fluid to pass through. An alignment rib 402 is disposed within an alignment channel 444 of the ferrule 440. A primary rib 404, a secondary rib 406, and a stop 408 are in substantial contact with the ferrule 440. The ribs 404, 406 and the stop 408 are compressed and deformed between the reducer 420 and the ferrule 440. The primary and secondary ribs 404, 406 form a seal from fluid flowing in a radial direction through the lumen created by the reducer 420, the ferrule 440, and the gasket 400. The positive stop 408 has a tapering surface 409 that is only partially in contact with the ferrule 440.

In various embodiments, an alignment rib may be positioned by a user toward a receiving alignment channel of a ferrule. An alignment rib may protrude farther from an outer surface of a gasket, and also may be thinner, than other outer surface protruding features of the gasket (e.g., a primary rib, a secondary rib, a positive stop, or the like) such that the alignment rib is the first feature to engage an alignment channel and so that the alignment rib is the only feature of a gasket that may interface into the alignment channel. In this way, an alignment rib may self-align with an opposing ferrule. A user may position an alignment rib into the alignment channel without the user touching the gasket (e.g., handling the reducer and/or ferrule(s) rather than the gasket). The alignment rib may not be compressed or may be minimally compressed as it may not act as a strong seal against a flow of fluid through a flow path. The alignment rib may easily enter an alignment channel such that a user may quickly and easily mate the gasket, the features of the gasket, and the ferrules together. Proper alignment in handling and installation of the components may be the best defenses against flow connection failure.

In various embodiments, a rib, such as a primary rib or a secondary rib, may create a seal when in contact with an opposing ferrule. The seal(s) is/are created by an axial force through the rib(s) that is substantially parallel with a flow lumen of the flow connection. A seal may resist a radial force from the flow lumen of a flow connector. An axial sealing force may be strengthened by compressing the rib(s) via, e.g., clamping the ferrules adjacent the rib(s). Additional seals (e.g., primary and secondary) may redundantly assist each other in preventing fluid from radially translating from a flow lumen to an atmosphere outside of the flow connector.

In various embodiments, a taper about an inner edge of a gasket may assist in sealing a flow connector. An inner surface of a taper may extend from a rib and taper radially inward toward a flow lumen of the flow connector and may also extend from the rib toward a rim of the ferrule that the gasket is disposed on. The taper meets the rim of the ferrule without a significant gap. The outer surface of the taper may be substantially continuous with an inner surface of the ferrule rim. This substantial lack of any gap makes the seal "hygienic" as there are no cervices that microorganisms may collect and grow in. The inner surface may be exposed to a significant amount of a radial pressure from a fluid flowing through the flow connector. The shape of the inner surface of the taper may assist in directing at least some of the fluid pressure toward one or more features of the ferrule rim rather than radially outward. Such a feature of the ferrule rim may be a ferrule rib about the flow lumen and in substantial contact with an outer surface of the taper. The ferrule rib may resist forces from the flow lumen that are translated to the outer surface of the taper from the inner surface of the taper. The outer surface of the taper may increase surface contact with the ferrule rib as pressure increases within the flow lumen.

In various embodiments, a gasket may be overmolded into a ferrule. Overmolding is a process where a single part is manufactured using two or more different materials in combination. The first material (e.g., a substrate) is partially or fully covered by one or more subsequent materials (overmold materials). Insert molding may include molding soft elastomers to rigid substrates that are held within molding tools that the soft elastomer may be injected into. Elastomers are adhesion bonded, which may include mechanical locks, chemical bonds, or other bonding. Adhesion about a substrate may be achieved by heating up the elastomer and/or the substrate sufficiently to melt the elastomer and/or at least the surface of the substrate to achieve a bond (e.g., a mechanical bond, a chemical bond, and/or the like). Two-shot molding may include two injections that may have a substrate that is injected first, followed by an elastomeric injection. The substrate may be heated to a semi-solid or gel state. Co-injection molding may include injecting the substrate and the elastomer into the same mold. The materials may be selected and controlled such that they flow and interact compatibly with each other. A substrate ferrule and an overmolded gasket may comprise various materials. A substrate may be manufactured via known manufacturing techniques for rigid polymers, metals, or ceramics such as machining, casting, injection molding, or the like. A gasket may be manufactured directly onto/into the substrate through a molding process for thermoplastic (such as injection molding for TPE/TPU/TPV) or elastomeric molding (such as LIM, compression, or transfer molding for thermoset elastomers). An overmold process results in the manufacturing of a single component that consists of two or more dissimilar materials. Dissimilar materials for a substrate ferrule and a gasket may allow for the benefits of, e.g., a rigid ferrule/reducer and a compliant gasket. A rigid reducer may allow for higher pressured fluid flow through a flow lumen of the reducer than a less-rigid reducer, e.g., a unibody silicone reducer that may strain, deform, or rupture in response to a higher pressure of fluid flow. A compliant gasket of a material dissimilar from the substrate ferrule/reducer may allow for a well-bonded fit between the substrate and the gasket and may also allow for a uniform compressible seal between ferrules for sealing about and/or against radial fluid flow forces from a flow lumen. Such dissimilar material advantages may not be enjoyed by a ferrule and gasket comprising an identical or similar material. An embodiment may be designed with reducer geometries that comply with the American Society of Mechanical Engineers Bioprocessing Equipment standards. Various embodiments may need to be sterilized before installation and between uses and re-uses. Materials may be selected such that the connection parts are functional after being subjected to sterilization techniques such as autoclaving, gamma or other radiation, or the like. The materials may be heat stable and structurally robust to withstand sterilization through multiple uses without losing aseptic qualities, sealing qualities, etc. A substrate for overmolding a gasket may be a reducer. The gasket may be overmolded in a position that is ideal for a sanitary connection to another ferrule of a desired connection size.

In various embodiments, a ferrule may include one or more retention features that increase adhesion between the ferrule and the gasket (e.g., the substrate and overmold, respectively) by increasing the surface area for the gasket to adhere too and/or features that allow for a mechanical interlock to hold the gasket in place. One or more retention cavities within a ferrule, fitting, and/or reducer may allow for an overmold material to flow into and about the cavities during manufacturing, and/or the cavities may allow for extensions of a gasket to snugly fit into. One or more cavities may provide more frictional surface area and an intimate co-mingling of the gasket with the ferrule. Such cavities make it more difficult for the gasket to be separate from the ferrule. Cavities may be positioned about a ferrule and may extend into a gasket channel at one end of each cavity, and out to the atmosphere at the other end of the cavity. The cavities may be arranged in an array about the ferrule such that they are substantially radially equidistant from each other for symmetrical retention of a gasket. Example nominations of cavity arrays about the ferrule may include 1, 2, 3, 4, 5, 6, 8, or 10 cavities, or the like. One or more cavities may not extend through the ferrule to the atmosphere, the cavity being enclosed on all sides except to the gasket channel. A cavity may increase in thickness as the cavity extends radially outward, which may allow for better retention as an overmolded gasket cures within the cavity because the larger portion of the molded gasket in the thicker portion of the cavity may not easily be pulled through the thinner portion of the cavity. A gasket may form one or more plugs within the cavity(ies) that anchor the gasket to the ferrule. A ferrule and/or a gasket channel may include one or more friction channels within the gasket channel that extend about the ferrule. These friction channels are sized and shaped to increase the surface area of the gasket channel. The additional surface area provided by the friction channels provides additional surface area for the gasket to interface with during installation and/or overmolding. The friction channels may be aligned concentrically adjacent each other to increase the amount of additional friction channel surface area per radial length of a gasket channel.

CONCLUSION

This disclosure has focused on a handful of discrete embodiments, with the intention of illustrating the principles of the systems and methods described. These descriptions are intended to be illustrative rather than limiting. Unless otherwise defined, all technical terms used herein have the same meaning as commonly understood by one of ordinary skill in the art to which the disclosure belongs.

As used herein, the terms "reducer," "fitting," and any plural derivative of these terms are meant to be interchangeable. Additionally, the term "ferrule" is meant to refer to a region of a reducer or fitting that is configured to meet, engage, interact, and/or mate with another body such as, e.g., a gasket, another ferrule, or the like. As such, features, uses, etc. described with reference to one or more of these terms are intended to apply to other references and embodiments of these terms unless clearly stated otherwise.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof. As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise. The term "or" is generally employed in its sense including "and/or" unless the content clearly dictates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effectuate such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art. Finally, while certain embodiments of the present invention are described herein. It is, however, expressly noted that the present invention is not limited to these embodiments, but rather the intention is that additions and modifications to what was expressly described herein are also included within the scope of the invention. Moreover, it is to be understood that the features of the various embodiments described herein are not mutually exclusive and can exist in various combinations and permutations, even if such combinations or permutations are not made expressly herein, without departing from the spirit and scope of the invention. In fact, variations, modifications, and other implementations of what is described herein will occur to those of ordinary skill in the art without departing from the spirit and the scope of the invention. As such, the invention is not to be defined only by the illustrative description herein.

What is claimed is:

1. A bioprocessing flow connection system comprising:
   a flow reducer comprising:
     a first end with a first aperture and a first diameter;
     a second end with a second aperture and a second diameter that is different than the first diameter;
     a reducer lumen extending through the first and the second end;
     a reducer rim about the first end and about the first aperture;
     a gasket channel in the reducer rim and extending about the first aperture;
     an overmold channel within the gasket channel, the overmold channel extending about the first aperture and toward the second end; and
     one or more cavities within the overmold channel extending radially away from the reducer lumen;
   a ferrule substantially aligned with the flow reducer comprising:
     a ferrule lumen through a ferrule aperture;
     a ferrule rim about the ferrule aperture; and
     an alignment channel about the ferrule rim; and
   a gasket disposed within the gasket channel, the gasket being overmolded within the gasket channel and extending within the one or more cavities, the gasket comprising:
     an alignment rib disposed on an outer surface of the gasket and extending about the first aperture, the alignment rib configured to substantially align with the alignment channel of the ferrule.

2. The bioprocessing flow connection system of claim 1, further comprising:
   a plurality of concentric friction channels within the reducer rim extending about the lumen; and
   wherein the gasket extends within the friction channels.

3. The bioprocessing flow connection system of claim 1, further comprising a stop disposed on the outer surface of the gasket and extending about an outer edge of the gasket, the stop having a surface tapering radially toward the reducer lumen.

4. The bioprocessing flow connection system of claim 1, further comprising:
   a process vessel having substantially aligned with the second end of the flow reducer; and
   wherein the ferrule is part of a filtration vessel.

5. A bioprocessing flow connection system comprising:
   a flow reducer comprising:
     a first end with a first aperture and a first diameter;
     a second end with a second aperture and a second diameter that is different than the first diameter;
     a reducer lumen extending through the first and the second end;
     a reducer rim about the first end and about the first aperture; and
     a gasket channel in the reducer rim and extending about the first aperture;
   a ferrule substantially aligned with the flow reducer comprising:
     a ferrule lumen through a ferrule aperture;
     a ferrule rim about the ferrule aperture; and
     an alignment channel about the ferrule rim; and
   a gasket disposed within the gasket channel comprising:
     an alignment rib disposed on an outer surface of the gasket and extending about the first aperture, the alignment rib configured to substantially align with the alignment channel of the ferrule;
     a primary rib disposed on the outer surface of the gasket concentrically within the alignment rib; and
     an inner surface of the gasket that tapers inwardly toward both of the reducer rim and the reducer lumen.

6. The bioprocessing flow connection system of claim 5, wherein the inner surface increases surface contact with the reducer rim as pressure increases within the lumen.

7. The bioprocessing flow connection system of claim 5, wherein the reducer rim includes a reducer rib about the first aperture in substantial contact with an outer surface of the inner surface of the gasket.

8. The bioprocessing flow connection system of claim 5, further comprising a secondary rib disposed on the outer surface of the gasket concentrically between the alignment rib and the primary rib.

9. A filtration system comprising:
- a flow reducer comprising:
  - a first rim about a lumen;
  - a gasket channel in the first rim and extending about the lumen;
  - an overmold channel in the first rim; and
  - one or more cavities in the overmold channel extending radially outward;
- a gasket overmolded within the first rim, the gasket extending within the one or more cavities;
- a ferrule substantially aligned with the gasket; and
- a clamp about the flow reducer and ferrule, the clamp compressing the flow reducer and ferrule toward each other.

10. The filtration system of claim 9, further comprising an alignment rib disposed on an outer surface of the gasket and extending about an aperture of the gasket, the alignment rib configured to substantially align with an alignment channel of the ferrule.

11. The filtration system of claim 9, further comprising:
- a primary rib disposed on an outer surface of the gasket;
- an inner edge of the gasket that tapers inwardly toward an inner edge of the first rim; and
- a secondary rib disposed on the outer surface of the gasket concentrically outside of the primary rib.

12. The filtration system of claim 9, wherein the reducer is disposed between a fluid feed and a tangential flow for hollow fiber filtration unit.

* * * * *